United States Patent
Chevalier et al.

(10) Patent No.: US 6,403,065 B1
(45) Date of Patent: Jun. 11, 2002

(54) OPTICAL BRIGHTENERS AS BLEACHING AGENTS

(75) Inventors: Véronique Chevalier, Villecresnes; Mélanie Quest, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/621,077

(22) Filed: Jul. 21, 2000

Related U.S. Application Data

(63) Continuation of application No. 09/311,737, filed on May 14, 1999, now Pat. No. 6,203,781.

(30) Foreign Application Priority Data

May 14, 1998 (FR) .............................................. 9806109

(51) Int. Cl.$^7$ .............................................. A61K 7/135
(52) U.S. Cl. ........................................... 424/62; 424/63
(58) Field of Search ................................ 424/400, 401, 424/70.1, 63, 64, 59, 62; 514/159, 844, 846, 945

(56) References Cited

U.S. PATENT DOCUMENTS

| | | | |
|---|---|---|---|
| 5,733,558 A | | 3/1998 | Breton et al. |
| 5,830,446 A | * | 11/1998 | Berthiaume et al. ....... 424/70.1 |
| 5,858,997 A | | 1/1999 | Crotty et al. |
| 5,880,076 A | | 3/1999 | Vermeer |
| 5,968,487 A | | 10/1999 | Galey et al. |

OTHER PUBLICATIONS

Database WPI, Section Ch, Week 9624, Derwent Publications Ltd., London, GB; An 96–235933, XP002098943 & JP 08 902053 A (Mikimoto Seiyaku KK), Apr. 9, 1996 (Abstract Only).

Database WPI, Section Ch, Week 9441, Derwent Publications Ltd., London, GB; An 94–329890, XP 002098944 & JP 06 256150 A (Maruzen Seiyaku KK), Sep. 13, 1994 (Abstract Only).

Database WPI, Section Ch, Week 9125, Derwent Publications Ltd., London, GB; An 91–181427, XP002098945 & JP 03 109343 A (Maruzen Kasei Co Ltd), May 9, 1991 (Abstract Only).

Database WPI, Section Ch, Week 8912, Derwent Publications Ltd., London, GB; An 89–088653, XP 002098946 & JP 01 038009 A (Pola Kasei Kogyo KK), Feb. 8, 1989 (Abstract Only).

Patent Abstracts of Japan, vol. 017, No. 561, (C–1119), Oct. 9, 1993, & JP 05 163115 A (Kanebo Ltd), Jun. 29, 1993 (Abstract Only).

Patent Abstracts of Japan, vol. 017, No. 674, (C–1140), Dec. 10, 1993, & JP 05 221845 A (Hisamitsu Pharmaceut Co Inc), Aug. 31, 1993 (Abstract Only).

Patent Abstracts of Japan, vol. 096, No. 009, Sep. 30, 1996, & JP 08 127525 A (Kanebo Ltd), May 21, 1996 (Abstract Only).

Database WPI, Section Ch, Week 9519, Derwent Publications Ltd., London, GB; An 95–144683, XP002098947 & JP 07 069859 A 9Shiseido Co Ltd), Mar. 14, 1995 (Abstract Only).

Chemical Abstracts, vol. 83, No. 19, Nov. 10, 1975, Columbus, Ohio, US; abstract No. 158891, XP002098962 & Forbes P.D. et al: Food Cosmetic Toxicol., vol. 13, No. 3, 1975, pp. 335–337, U.S.A. (Abstract Only).

* cited by examiner

*Primary Examiner*—Deborah D. Carr
(74) *Attorney, Agent, or Firm*—Oblon, Spivak, McClelland, Maier & Neustadt, P.C.

(57) ABSTRACT

Methods and compositions for bleaching the skin are provided. Compounds of the optical brightener family may be applied in an effective amount to bleach the skin. The present inventions also relates to compositions which contain of compounds of the optical brightener family and other cosmetic compounds, such as skin bleaching agents, screening agents, anti-wrinkle agents and moisturizers.

7 Claims, No Drawings

OPTICAL BRIGHTENERS AS BLEACHING AGENTS

This is a Continuation of application Ser. No. 09/311,737 filed on May 14, 1999, now U.S. Pat. No. 6,203,781.

BACKGROUND OF THE INVENTION

1. Field of the Invention

The present invention relates to the use of compounds of the optical brightener family in a cosmetic composition or for the preparation of a dermatological composition, for topical application. The composition imparts greater uniformity, greater homogeneity greater clarity, an alabaster-smooth appearance and greater whiteness to the complexion of the skin. Such compositions may also have shadow-concealing properties.

The invention also relates to the compositions which contain compounds of the optical brightener family in combination with other cosmetically useful compounds, such as skin bleaching agents, screening agents, anti-wrinkle agents and moisturizers.

Additionally, the present invention relates to a process for the immediate bleaching of the skin, by applying to the skin a cosmetic composition comprising at least one compound of the optical brightener family.

2. A Description of the Background

It is common for people with colored or even dark skin to wish to lighten the skin, and, with this aim, to use cosmetic or dermatological compositions containing bleaching agents.

The substances most commonly used as bleaching agents are hydroquinone and its derivatives, kojic acid and derivatives thereof, azelaic acid, arbutin and derivatives thereof, alone or in combination with other active agents.

Such compositions comprising bleaching agents are also used by individuals whose skin displays dyschromias. These dyschromias are of diverse origin: age (age marks), exposure to UV radiation, pregnancy mask, skin pathology, etc.

However, these agents are not without drawbacks. In particular, it is necessary to use them for a long period and in large amounts in order to see a bleaching effect on the skin. No immediate effect is observed when compositions containing them are applied.

In addition, hydroquinone and its derivatives are used in an amount which is effective to observe a bleaching effect. In particular, hydroquinone is known for its cytotoxicity towards melanocytes.

Moreover, kojic acid and its derivatives have the drawback of being expensive and, for this reason, of not being able to be used in large amounts in products for mass marketing.

It is known practice to use cosmetic compositions which are capable of making the complexion uniform and optionally of giving an immediate white appearance, these compositions consisting of powders dispersed in a binder. The powders generally contain white or colored pigments depending on the desired effect, and fillers in lamellar form, or alternatively silica in the form of platelets. The uniforming effect on the complexion is obtained essentially by virtue of the covering power provided by the fillers in lamellar form.

The drawback of such compositions is that the smoothing out of the skin's defects is provided by the covering power of the compositions. Skin bearing make-up in this way loses its natural appearance on account of the lack of clarity of these compositions.

Although it has been possible to consider using lamellar fillers as a means for increasing the clarity of these compositions (see for example U.S. Pat. No. 4,899,163), they have the drawback of acting by reflecting light and give the skin an unnatural shiny appearance.

There is, therefore, still a need for cosmetic and/or dermatological compositions for obtaining a homogeneous, uniform, white complexion of natural appearance, where these compositions having satisfactory clarity after they have been applied to the skin.

French patent application FR-2,741,261 describes cosmetic compositions comprising a brightening fluorescent agent, these agents also known as optical brighteners. These agents have the advantage of intensifying the radiance and brightening the colors of cosmetic compositions comprising them when they are applied to the skin or the hair. The effect of these agents is observed on a colored support (the hair) or in a colored composition (make-up such as mascara, nail varnish or lipstick). However, the effect of optical brighteners on the skin itself as described above is neither disclosed nor suggested therein.

SUMMARY OF THE INVENTION

It is an object of the present invention to provides methods and compositions for bleaching the skin.

This object, and others, may be accomplished with a method of bleaching skin by applying to the skin an effective amount of at least one compound belonging to the optical brightener family.

The object of the invention may also be accomplished with a composition containing at least one compound belonging to the optical brightener family and at least one second skin bleaching agent which is not an optical brightener.

A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

The subject of the invention is the use of at least one compound belonging to the optical brightener family, in a composition or for the preparation of a composition intended for bleaching the skin, in particular for the immediate bleaching of the skin. Such a composition gives the complexion greater uniformity, greater homogeneity, greater clarity and all alabaster-smooth appearance.

Such a use is particularly effective on Asian skin. Alternatively, Caucasian skin may be treated.

More particularly, this composition is a cosmetic composition. Use of the composition for dermatological applications is also within the scope of the invention.

The compositions according to the invention are preferably skincare compositions rather than make-up compositions or compositions intended to be applied to the hair.

A subject of the invention is also the use of at least one compound belonging to the optical brightener family in a composition or for the preparation of a composition which is effective on Caucasian skin.

Optical brighteners are compounds which are well-known to those skilled in the art. Such compounds are described in "Fluorescent Whitening Agent, Encyclopedia of Chemical Technology, Kirk-Othmer", Vol. 11, pp.227–241, 4th edition, 1994, Wiley, incorporated herein by reference. Optical brighteners can be defined more particularly as compounds which absorb in the UWA range between 300 and 390 nm and re-emit essentially between 400 and 525 nm.

Among the optical brighteners, particularly preferred examples are stilbene derivatives, coumarin derivatives, oxazole and benzoxazole derivatives and imidalzole-derivatives. Such compounds are readily commercially available. For example, Tinopal SOP® and Uvitex OB® are sold by Ciba Geigy. The optical brighteners preferably utilized the present invention are sodium 4,4'-bis[(4,6-dianilino-1,3,5-triazin-2-yl)amino]stilbene-2,2'-disulphonate and 2,5-thiophenediylbis(5-tert-butyl-1,3-benzoxazole).

A subject of the invention is also the use of at least one compound of the optical brightener family in a composition or for the preparation of a composition as a skin bleaching agent, in particular as an immediate bleaching agent, and/or as an agent intended to give the skin at least one of the properties chosen from: uniformity, homogeneity, clarity and an alabaster-smooth appearance.

A subject of the invention is also the use of at least one compound of the optical brightener family in a composition or for the preparation of a composition as a concealer.

Thus, the shadows around the eyes, observed by the presence of a darker, or even grey or black, surface around the eyes and/or by the presence of bags under the eyes and/or by a withered appearance of the contour of the eyes, can be reduced or even disappear by applying the composition according to the invention thereto.

Optical brighteners are preferably used according to the present invention in an amount ranging from 0.1 to 15% by weight, and even more preferably from 0.5 to 10% by weight, relative to the total weight of the composition. These weight % ranges include all specific values and subranges therebetween, including 0.2, 1, 2, 5, 8 and 12% by weight.

The optical brighteners are advantageously combined with other cosmetic agents with which they have a reinforced or complementary action.

Thus, a subject of the invention is a composition, more particularly a cosmetic composition, comprising at least one compound of the optical brightener family and at least one other bleaching agent and/or depigmenting agent conventionally used in cosmetics.

Among these bleaching agents and/or depigmenting agents conventionally used in cosmetics, it is preferred to use hydroquinone and derivatives thereof, such as hydroquinone monomethyl ether and hydroquinone monoethyl ether, kojic acid and derivatives thereof, lactic acid and salts thereof, ascorbic acid and derivatives thereof, azelaic acid, arbutin and derivatives thereof, L-2-oxothiazolidine-4-carboxylic acid (as described in patent EP 0,780,120, incorporated herein by reference), paracetamol, as described in the French patent application filed on Dec. 6, 1996, Ser. No. 96/15046, incorporated herein by reference, and aminophenol derivatives containing a carbamate, urea or sulphonamide function of formula (I), as described in the French patent application filed on Aug. 8, 1997, Ser. No. 97/10710, incorporated herein by reference. These aminophenol derivatives have the formula (I) below:

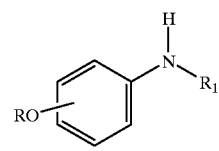

(I)

in which:

R represents a hydrogen atom or a radical —$COR_2$, $R_2$, which may be identical or different, representing a radical chosen from a saturated or unsaturated, linear, cyclic or branched, optionally hydroxylated, $C_1$ to $C_{30}$ alkyl or alkoxy radical, $R_1$ is chosen from a radical of formula (a), (b) or (c) below;

(a) —CO—$NR_3R_4$ (b) —CO—O—$R_5$ (c) —$SO_2$—$R_5$ $R_3$ represents a hydrogen atom or a linear or branched, saturated or unsaturated, optionally hydroxylated $C_1$ to $C_6$ alkyl radical, $R_4$ represents a hydrogen atom or the radical $R_5$ defined below, $R_5$ represents a radical chosen from a saturated or unsaturated, linear, cyclic or branched, optionally hydroxylated, $C_1$ to $C_{30}$ alkyl radical.

Among these aminophenol derivatives containing a carbonate, urea or sulphonamide function of formula (I), the compounds more particularly preferred are N-ethyloxycarbonyl4-aminophenol; N-ethyloxycarbonyl-O-ethyloxycarbonyl-4-aminophenol; N-cholesteryloxycarbonyl-4-aminophenol and N-ethylaminocarbonyl-4-aminophenol.

The invention also relates to the use of such a composition for the purpose of obtaining both short-term and long-term bleaching of the skin. Such a composition also preferably comprises at least one agent capable of screening out UV rays and/or at least one desquamating agent.

Another embodiment of the present invention is a composition, more particularly a cosmetic composition, comprising at least one compound of the optical brightener family and at least one agent capable of screening out UV rays and/or at least one desquamating agent. Among the agents capable of screening out UV rays, hydrophilic or lipophilic organic screening agents may be used effectively in the present invention.

The hydrophilic screening agents can be chosen in particular from benzophenone derivatives, p-aminobenzoic acid derivatives, camphor derivatives or benzimidazole derivatives. The hydrophilic screening agents can be present in the final composition according to the invention at a content which can range from 0.1 to 20%, preferably from 0.2 to 10%, by weight relative to the total weight of the composition. These weight % ranges include all specific values and subranges therebetween, including 0.2, 1, 2, 5, 8, 12 and 15% by weight.

The lipophilic screening agents which are particularly suitable for the present invention can be chosen from dibenzoylmethane derivatives, benzimidazole derivatives, cinnamic derivatives, salicylic derivatives, camphor derivatives, triazine derivatives, benzophenone derivatives, β,β-diphenylacrylate derivatives, p-aminobenzoic acid derivatives, and the screening polymers and screening silicones described in WO-93/04665 and WO-94/06404. Other examples of organic screening agents are given in EP-A-0,487,404. Each of these publications is incorporated herein by reference.

The lipophilic screening agent(s) can be present in the final composition according to the invention at a content which can range from 0.5 to 30%, preferably from 0.5 to 20%, by weight relative to the total weight of the composition. These weight % ranges include all specific values and subranges therebetween, including 0.2, 1, 2, 5, 8, 12, 15, 18 and 25% by weight.

The inorganic screening agents can be pigments or nanopigments (average size of the primary particles: generally between 5 nm and 100 nm, preferably between 10 and 50 nm) of coated or uncoated metal oxides, such as, for example, nanopigments of titanium oxide (amorphous or crystallized in rutile and/or anatase form), iron oxide, zinc oxide, zirconium oxide or cerium oxide, which are all photoprotective agents that are well known per se, which act by physically blocking (reflection and/or scattering) UV radiation. Conventional coating agents are, moreover, alumina and/or aluminium stearate, and silicones. Such coated or uncoated metal oxide nanopigments are described in particular in patent applications EP-A-0,518,772 and EP-A-0,518,773, each incorporated herein by reference.

The inorganic screening agents can be present in the final composition according to the invention at a content which can range from 0.1 to 20%, preferably from 0.2 to 10%, by weight relative to the total weight of the composition. These weight % ranges include all specific values and subranges therebetween, including 0.5, 1, 2, 5, 8, 12 and 15% by weight.

Among the desquamating agents, mention may be made of hydroxy acids, more particularly α- and β-hydroxy acids, salicylic acid or a derivative thereof, which may be salified, natural or synthetic retinoids, such as retinol, retinol esters, retinoic acid or retinal. As salicylic acid derivatives, mention may be made in particular of those described in FR-A-2,581,542 and EP-A-378,936, each incorporated herein by reference, and in particular 5-n-octanoylsalicylic acid, 5-n-decanoylsalicylic acid, 5-n-dodecanoylsalicylic acid, 5-n-octylsalicylic acid, 5-n-heptyloxysalicylic acid, 4-n-heptyloxysalicylic acid and quaternary ammonium salts thereof, such as the dimethylhydroxypropylarnnonium salts. The salicylic acid derivatives described in EP-A-570,230, incorporated herein by reference, can also be used.

Another embodiment of the present invention is a composition, more particularly a cosmetic composition, comprising at least one optical brightener and at least one moisturizer. Such a composition is particularly effective in preventing and/or treating shadows under the eyes.

Among the moisturizers which can be used in these composition, mention may be made in particular of urea or its derivatives and polyols such as, for example, glycerol, sorbitol or propylene glycol.

The invention also relates to a composition, preferably a cosmetic composition, comprising at least one optical brightener and at least one anti-wrinkle agent. Such a composition is, in this case also, particularly suitable for preventing and/or treating shadows under the eyes.

Among the anti-wrinkle agents which can be used in these compositions, mention may be made in particular of: hydroxy acids, more particularly α- and β-hydroxy acids, ascorbic acid or its derivatives, salicylic acid or one of its derivatives, which may be salified, natural or synthetic retinoids, such as retinol, retinol esters, retinoic acid or retinal. As salicylic acid derivatives, mention may be made in particular of those described in FR-A-2,581,542 and EP-A-378,936, and in particular 5-n-octanoylsalicylic acid, 5-n-decanoylsalicylic acid, 5-n-dodecanoylsalicylic acid, 5-n-octylsalicylic acid, 5-n-heptyloxyslicylic acid, 4-n-heptyloxysalicylic acid and the quaternary ammonium salts thereof, such as the dimethylhydroxypropylamnmonium salts. The salicylic acid derivatives described in document EP-A-570,230, incorporated herein by reference, can also be used.

Another aspect of the present invention is a process for the immediate bleaching of the skin, comprising applying to the skin a cosmetic composition comprising at least one optical brightener.

The compositions containing the optical brighteners used according to the invention can be in any pharmaceutical form normally used for topical application, for example in the form of solutions, gels, dispersions of the lotion or serum type, emulsions of liquid or semi-liquid consistency of the milk type, obtained by dispersing a fatty phase in an aqueous phase (O/W) or, conversely, (W/O), or suspension or emulsions of soft, semi-solid or solid consistency of the cream or gel type, or alternatively microemulsions, microcapsules, microparticles or vesicle dispersions of ionic and/or nonionic type. These compositions may be prepared according to well-known methods.

The compositions, mote particularly the cosmetic compositions, of the invention can contain adjuvants that are common in the cosmetics field, such as emulsifiers, hydrophilic or lipophilic gelling agents, hydrophilic or lipophilic active agents, preserving agents, antioxidants, fragrances, fillers and dyestuffs. The amounts of these various adjuvants are those conventionally used in the cosmetics field, and, for example, from 0.01 to 20% of the total weight of the composition. This range includes all specific values and subranges therebetween, such as 0.02, 0.05, 1, 2, 5, 8, 10 and 15% by weight. Depending on their nature, these adjuvants can be introduced into the fatty phase, into the aqueous phase and/or into the lipid vesicles.

Water-in-oil (W/O) or oil-in-water (O/W) emulsifiers can be used as emulsifiers, depending on the desired final emulsion.

As emulsifiers, mention may be made, for example, of the mixture of glyceryl/stearate/PEG-100 stearate (Arlacel 165 sold by ICI), PEG-20 stearate (Myrj 49 sold by ICI), PEG-40 stearate (Myrj 52 sold by ICI) and sorbitan tristearate (Span 65 sold by ICI).

The emulsifier content can range from 0.1 to 15% by weight, and preferably from 0.5 to 5% by weight, relative to the total weight of the composition. These weight ranges include all specific values and subranges therebetween, including 0.2, 1, 2, 8, 10 and 12% by weight.

Co-emulsifiers can be added to the composition according to the invention, for example in an amount ranging from 0.05% to 10% by weight relative to the total weight of the composition, inclusive full specific ranges and subranges therebetween, such as 1, 2, 3, 5 and 8% by weight. Glyceryl stearate may be used as a co-emulsifier.

In the lipid vesicle dispersions, the emulsifier can consist of the vesicles themselves or of ionic and/or nonionic lipids.

As oils which can be used in the invention, mention may he made of mineral oils, plant oils (corn germ oil), synthetic oils (isohexadecane), silicone oils (cyclomethicone) and fluoro oils. Fatty alcohols (stearyl alcohol, cetyl alcohol), fatty acids (stearic acid) and waxes can also be used.

Hydrophilic active agents which can be used, for example, are proteins or protein hydrolysates, amino acids, urea, allantoin, sugars and sugar derivatives, and glycyrrhetinic acid.

Lipophilic active agents which can be used are tocopherol (vitamin E) and its derivatives, essential fatty acids, ceramides and essential oils.

These compositions in particular constitute treatment or care creams for the face, for the hands or for the body, protective or care body milks or lotions, gels or mousses for skincare or skin treatment.

For bleaching the skin, the compositions described above may be applied in an amount effective for skin bleaching to the surface of the skin. The compositions of the invention may be applied as often as necessary or desired to provide the skin with the desired complexion. For example, the compositions of the invention may be applied daily.

Having generally described this invention, a further understanding can be obtained by reference to certain specific examples which are provided herein for purposes of illustration only and are not intended to be limiting unless otherwise specified.

EXAMPLES

In the following examples, the proportions indicated are percentages by weight

Example 1

O/W Fluid Cream

| | |
|---|---|
| 2-Ethylhexyl palmitate | 8% |
| Liquid Petroleum jelly | 8% |
| Glyceryl mono/diisostearate | 2% |
| Mixture of glyceryl mono/distearate, stearic acid and glycerol (40/501515) | 2% |
| Sodium 4,4'-bis[(4,6-dianilino-1,3,5-triazin-2-yl)amino]stilbene-2,2'-disulphonate* | 1% |
| Triethanolamine | 0.9% |
| Propylene glycol | 2% |
| Stearic acid | 2% |
| Magnesium stearate | 2% |
| Preserving agents | qs |
| Water | qs 100 |

*Tinopal SOP ® sold by Ciba Geigy

Example 2

O/W Fluid Cream

A cream is prepared with the same constituents as in Example 1, except that the stilbene derivative is replaced with 1% of 2,5-thiophenediylbis(5-tert-butyl-1,3-benzoxazole) sold by Ciba Geigy under the trade name Uvitex OB®.

These two creams were tested on Asian women and were very much appreciated on account of their immediate bleaching effect and their clarity. These two creams give the skin an alabaster-smooth appearance.

Example 3

Concealer Cream for Around the Eyes

| | |
|---|---|
| Sodium hyaluronate | 0.1% |
| Sodium 4,4'-bis[(4,6-dianilino-1,3,5-triazin-2-yl)amino]stilbene-2,2'-disulphonate* | 7% |
| Crosslinked acrylamidomethylpropanesulphonic acid partially neutralized with aqueous ammonia | 1.5% |
| Glycerol | 5% |
| Ethyl alcohol | 5% |
| Oxyethylenated methylglucose dioleate (120 EO) | 0.5% |
| Oxyethylenated sorbitan monolaurate (20 EO) | 0.5% |
| Preserving agents | qs |
| Water | qs 100 |

*Tinopal SOP sold by Ciba Geigy

Example 4

Concealer Cream for Around the Eyes

Example 3 was repeated with only 1% of Tinopal SOP.

The two concealer compositions of Examples 3 and 4 were tested on women with Caucasian skin. Both produce an immediate, natural and discrete shadow-concealing effect: unified coloration of the facial skin, appearance of the marks faded, withered appearance around the eyes attenuated.

Obviously, numerous modifications and variations of the present invention are possible in light of the above teachings. It is therefore to be understood that within the scope of the appended claims, the invention may be practiced otherwise than as specifically described herein.

French patent application serial No. 98-06109, filed on May 14, 1998, is incorporated a herein by reference.

What is claimed is:

1. A composition, comprising at least one optical brightener and at least one second skin bleaching agent which is not an optical brightener.

2. The composition of claim 1, wherein the second skin bleaching agent is selected from the group consisting of hydroquinone and derivatives thereof, kojic acid and derivatives thereof, lactic acid and salts thereof, ascorbic acid and derivatives thereof, azelaic acid, arbutin and derivatives thereof, L-2-oxothiazolidine-4-carboxylic acid, and paracetamol.

3. The composition of claim 1, wherein the second skin bleaching agent is represented by formula (I):

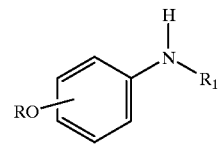

(I)

wherein

R is a hydrogen atom or —$COR_2$, $R_2$ is a saturated or unsaturated, linear, cyclic or branched, optionally hydroxylated, $C_1$ to $C_{30}$ alkyl or alkoxy radical, $R_1$ is a radical selected from the group consisting of (a) —CO—$NR_3R_4$, (b) —CO—O—$R_5$, and (c) —$SO_2$—$R_5$, $R_3$ is a hydrogen atom or a linear or branched, saturated or unsaturated, optionally hydroxylated, $C_1$ to $C_6$ alkyl radical, $R_4$ is a hydrogen atom or the radical $R_5$ defined below, $R_5$ is a saturated or unsaturated, linear, cyclic or branched, optionally hydroxylated, $C_1$ to $C_{30}$ alkyl radical.

4. The composition of claim 1, further comprising at least one UV screening agent and/or at least one desquamating agent.

5. A composition, comprising at least one optical brightener and at least one desquamating agent.

6. A composition, comprising at least one optical brightener and at least one moisturizer.

7. A composition, comprising at least one optical brightener and at least one anti-wrinkle agent.

* * * * *